United States Patent [19]

VanRheenen et al.

[11] Patent Number: 4,704,455

[45] Date of Patent: * Nov. 3, 1987

[54] 16α-METHYLATED Δ17(20)-CORTICOIDS

[75] Inventors: Verlan H. VanRheenen, Portage; Joel E. Huber, Texas Township, Kalamazoo County, both of Mich.

[73] Assignee: The Upjohn Company, Kalamazoo, Mich.

[*] Notice: The portion of the term of this patent subsequent to Feb. 4, 2003 has been disclaimed.

[21] Appl. No.: 724,380

[22] Filed: Apr. 18, 1985

Related U.S. Application Data

[63] Continuation-in-part of Ser. No. 618,986, Jun. 11, 1984, abandoned.

[51] Int. Cl.$^4$ ............................................. C07J 1/00
[52] U.S. Cl. .................................. 540/87; 260/397.3; 260/397.47; 260/397.5
[58] Field of Search .................... 260/239.55 R, 397.4, 260/397.45, 397.3, 397.47, 397.5; 540/87

[56] References Cited

U.S. PATENT DOCUMENTS

| | | | |
|---|---|---|---|
| 2,864,834 | 12/1958 | Mendelsohn et al. | 260/397.45 |
| 3,072,686 | 1/1963 | Wettstein et al. | 260/397.4 |
| 3,210,341 | 10/1965 | Lincoln et al. | 260/239.55 |
| 3,231,568 | 1/1966 | Julian et al. | 260/239.55 |
| 3,513,163 | 5/1970 | Brown | 260/239.55 |
| 3,700,660 | 10/1972 | Hempel et al. | 260/239.55 |
| 3,839,369 | 10/1974 | Hofmeister et al. | 260/397.45 |
| 3,876,633 | 4/1975 | Loken | 260/239.45 |
| 4,031,080 | 6/1977 | Palladino | 260/239.55 |
| 4,036,831 | 7/1977 | Loken et al. | 260/397.45 |
| 4,277,409 | 7/1981 | Warnant | 260/397.45 |
| 4,568,492 | 2/1986 | Walker | 260/239.55 R |

FOREIGN PATENT DOCUMENTS 2001990 2/1979 United Kingdom.

OTHER PUBLICATIONS

Organic Reactions in Steroid Chemistry, vol. II, J. Fried and J. A. Edwards, Van Nostrand Reinhold Co., NY 1972, pp. 75–76.
J. Am. Chem. Soc. 80, 3160–3161 (1958).
J. Am. Chem. Soc. 80, 4428 (1958).

*Primary Examiner*—Leonard Schenkman
*Assistant Examiner*—Joseph A. Lipovsky
*Attorney, Agent, or Firm*—Bruce Stein

[57] ABSTRACT

$C_{16}$-unsaturated corticoids are readily transformed to the corresponding 16α-methyl-17α-hydroxy corticoids by use of a $\Delta^{17(20)}$-20-silyl ether.

9 Claims, No Drawings

16α-METHYLATED Δ17(20)-CORTICOIDS

BACKGROUND OF THE INVENTION

The present application is a continuation-in-part of co-pending application Ser. No. 618,986, filed June 11, 1984, now abandoned.

Corticoids with a 16α-methyl group are known to be useful anti-inflammatory agents. These include dexamethasone (9α-fluoro-11β,17α,21-trihydroxy-16α-methylpregna-1,4-diene-3,20-dione), flumethasone (6α,-9α-difluoro-11β,17α,21-trihydroxy-16α-methylpregna-1,4-diene-3,20-dione) and paramethasone (6α-fluoro-11β,17α,21-trihydroxy-16α-methylpregna-1,4-diene-3,20-dione).

The 16-unsaturated corticoid (I) starting materials are known, see, U.S. Pat. Nos. 2,864,834, 3,210,341, 3,839,369, 4,031,080 and 4,277,409.

The transformation of 16-unsaturated pregnanes to 16α-methyl pregnanes by use of a Grignard reagent is known. The conjugate addition of a 16α-methyl group to a 16-unsaturated-20-keto steroid by means of a methyl Grignard reagent in the presence of a copper salt catalyst is well known, see Organic Reactions in Steroid Chemistry, Vol. II, J. Fried and J. A. Edwards, Van Nostrand Reinhold Co., NY, 1972, p 75. The product of such a reaction is the 16α-methyl-α$^{17(20)}$-20-enolate, which according to Fried may be trapped as the 20-acetate, see p 76. While the addition can go 1,2 or 1,4 with a ratio of about 1:1, the addition of cuprous chloride gave exclusively 1,4-addition in yields of greater than 90%.

U.S. Pat. No. 3,231,568 (JULIAN) discloses the transformation of a 16-unsaturated progesterone to the corresponding 17α-hydroxy-16α-methylprogesterone. However, JULIAN's pregnane did not have a second α/β-unsaturated ketone in the form of a Δ$^4$-3-ketone or Δ$^{1,4}$-3-ketone as the steroid A-ring was 3,5-cyclo. In addition, JULIAN disclosed a progesterone having no C$_{21}$ functionality while the process of the present invention uses a 21-acylate which is sensitive to the Grignard reaction and is hydrolyzable. The C-ring of JULIAN contained no substitution and therefore was not sensitive to the oxidation reaction conditions. A further distinction is that JULIAN traps with acetate and the enol acetate of JULIAN is not reactive to the mild peracid conditions of the present process and hence would not form the desired 17,20-epoxide (III).

U.S. Pat. No. 4,031,080 (PALLADINO) uses copper for the conjugate addition reaction but produces an enol acetate which as JULIAN would be unreactive to the mild and selective peracid reaction conditions of this invention producing the desired 17,20-epoxide (III). PALLADINO produces 17α-bromo-16α-methyl corticoid not a 17α-hydroxy-16α-methyl corticoid.

U.S. Pat. No. 4,277,409 (WARNANT) transforms a 16-unsaturated-21-acetate to a 16α-methyl-21-acetate, without introducing the necessary 17α-hydroxyl group while the process of the present invention introduces the desired 17α-hydroxyl group.

Great Britain Pat. No. 2,001,990 discloses a process to transform a 16-unsaturated corticoid (I) to the corresponding 16α-methyl corticoid (V) by methylating the 16-unsaturated corticoid with copper catalyzed methyl grignard to produce the 16α-methyl-Δ$^{17(20)}$-20-(magnesium bromide)enolate, followed by conversion by oxygenation to a 17α-hydroperoxide which is reduced to the corresponding 16α-methyl-17α,21-dihydroxy-20-one 21-acetate. The process of the present invention does not produce a 17α-hydroperoxide, but rather utilizes a 17α,20-epoxide (III) intermediate.

U.S. Pat. No. 3,072,686 (WETTSTEIN) discloses the transformation of a 16-unsaturated progesterone to a 17α-hydroxy-16α-methylprogesterone by reacting the 16-unsaturated progesterone with a Grignard reagent and cuprous chloride. WETTSTEIN produces a Δ$^{17(20)}$-20-enol acetate which is not reactive to the mild and selective peracid conditions of the present process and hence would not form the desired 17,20-epoxide (III).

Both J. Am. Chem. Soc. 80, 3160 (1958) and J. Am. Chem. Soc. 80, 4428 (1958) report the transformation of a 16-unsaturated progesterone to a 16α-methylprogesterone by use of a Grignard reagent followed by peracid oxidation to introduce the 17α-hydroxy group producing a 17α-hydroxy-16α-methylprogesterone. The 17α-hydroxy-16α-methylprogesterone is brominated and acylated to form the 21-acetoxy-17α-hydroxy-16α-methyl steroid.

U.S. Pat. No. 3,700,660 discloses a process of converting a 20-acyloxy-17,20-epoxy steroid to a 17α-acyloxy-20-keto steroid by use of a strong acid. U.S. Pat. No. 3,700,660 (HEMPEL) uses 20-acetate where the process of the present invention uses 20-silyl. The significance of this is that the Δ$^{17(20)}$-20-enol silane (II) of the present invention is much more reactive than the corresponding 20-acylate of HEMPEL which permits epoxidation of the Δ$^{17(20)}$ double bond in steroids having other double bonds such as Δ$^4$-3-keto, Δ$^{1,4}$-3-keto, Δ$^{9(11)}$-etc. whereas the 20-acylate of HEMPEL is limited to a non-functionalized steroid.

U.S. Pat. Nos. 3,513,163 and 4,036,831 disclose C$_{21}$ and C$_{11}$ trimethylsiloxy ethers respectively. Δ$^{17(20)}$-20-O-substituted steroids are known where the substituent is an acyl group or a Grignard substituent (—Mg—X), see U.S. Pat. Nos. 3,072,686, 3,231,568 and 4,031,080. This Mg—X substituted compound while disclosed is not isolatable.

17α,20-Epoxy-16α-methyl-20-O-substituted steroids are disclosed in U.S. Pat. No. 3,876,633 where the 20-O-substituent is an acyl group, see Claim 9.

Selective epoxidation of the Δ$^{9(11)}$ double bond over the Δ$^{16}$ double bond in a Δ$^{9(11)}$, $^{16}$-diene is set forth in U.S. Pat. No. 3,876,633. U.S. Pat. No. 3,876,633 discloses 9β,11β-epoxy-Δ$^{16}$-steroids where the A-ring is reduced. 9β,11β-epoxy-6α-fluoro-21-hydroxypregna-1,4,16-triene-3,20-dione 21-acetate is disclosed in U.S. Pat. No. 3,210,341, Example 9(b).

U.S. Pat. No. 4,036,831 discloses a process of protecting the 11β-hydroxyl group of a steroid, during subsequent reactions, with trimethylsilyl and the subsequent removal of the trimethylsilyl group by hydrolysis with 40-60% aqueous hydrogen fluoride.

SUMMARY OF THE INVENTION

Disclosed are the Δ$^{17(20)}$-steroid (II A-C), a 17α,20-epoxide (III A-C) and the 17α-silyl ether (IV A-C).

Further disclosed is a process for the preparation of a Δ$^{17(20)}$-steroid (II A-C) which comprises starting with a 16-unsaturated corticoid (I A-C) and (1) contacting the 16-unsaturated corticoid (I A-C) with a methylating agent in the presence of a copper catalyst and (2) contacting the product of step (1) with a silylating agent.

Also disclosed is a process for the preparation of a 17α,20-epoxide (III A-C) which comprises starting with a $\Delta^{17(20)}$-steroid (II A-C) and contacting it with a peracid.

DETAILED DESCRIPTION OF THE INVENTION

The 16-unsaturated corticoid (I A-C) starting materials are well known to those skilled in the art or can be readily prepared from known steroids by methods well known to those skilled in the art, see, for example, U.S. Pat. Nos. 2,773,080, 2,864,834, 3,210,341, 3,441,559, 3,461,144, 3,493,563, 3,839,369, 4,031,080, and 4,277,409.

The C$_3$ functionality of the $\Delta^4$-3-keto (A), $\Delta^{1,4}$-3-keto (B) and 3$\beta$-hydroxy-$\Delta^5$-(C) steroid does not have to be protected for the processes of the present invention. The 3$\beta$-hydroxy-$\Delta^5$-(C) steroid can have its C$_3$-hydroxyl group (Ca) protected as the silyl ether (Cb), ether (Cc) or ester (Cd), see Chart C. The free hydroxyl group (Ca) can be protected as the ether (Cc) or ester (Cd) as is well known to those skilled in the art. See Protective Groups in Organic Synthesis, Theodora W. Greene, Wiley & Sons, New York 1981. The ethers (Cc) are prepared by methods well known to those skilled in the art, see Steroid Reactions, Edited by Carl Djerassi, Holden-Day, San Francisco 1967, p 76–82. If the free 3$\beta$-hydroxyl group (Ca) is not protected as the ether (Cc) or ester (Cd) during the silation reaction, the free hydroxy group will be silated to form the silyl ether (Cb). During the silylation reaction, if the 3$\beta$-hydroxyl group is free and will be silylated, one additional equivalent of Grignard and silylating agent will be consumed. The C$_3$ protected forms of the 3$\beta$-hydroxy steroids (C) are considered equivalent to the non-protected or free form (C) respectively since the C$_3$ protecting groups are readily removable to convert the C$_3$ protected forms (Cb, Cc and Cd) to (A and C). The protecting group remains on until the hydrolysis (acid or base) of the 17$\alpha$,20-epoxide. If acid hydrolysis is utilized and the C$_3$ protecting group is acid labile (Cb and Cc) it will be removed. Likewise if base hydrolysis is utilized and the C$_3$ protecting group is base-sensitive (Cd) it wil be removed. If the C$_3$ protecting group is not sensitive to the hydrolysis agent, the C$_3$ protected steroid will have to be treated with the appropriate agent to remove the C$_3$ protecting group.

It is preferred that the 16-unsaturated corticoid (I A-C) be a $\Delta^4$-3-keto (A) or a $\Delta^{1,4}$-3-keto (B) corticoid, more preferably a $\Delta^{1,4}$-3-keto (B) corticoid. It is preferred that the 16-unsaturated corticoid have the C-ring $\Delta^{9(11)}$ or 9$\beta$,11$\beta$-epoxy. It is more preferred that the C-ring be 9$\beta$,11$\beta$-epoxy. It is preferred that R$_6$ be a hydrogen or fluorine atom, more preferred that R$_6$ be a hydrogen atom.

While it is preferred that the C-ring is $\Delta^{9(11)}$ or 9$\beta$,11$\beta$-epoxy, the C-ring can be converted to the desired 9$\alpha$-fluoro-11$\beta$-hydroxy functionality prior to the Grignard addition of the methyl group to the $\Delta^{16}$ double bond. If this is done, the 11$\beta$-hydroxy group should be protected as is well known to those skilled in the art, see for example, U.S. Pat. No. 4,036,831 where the protecting group is trimethylsilyl. Following the formation of the desired 16$\alpha$-methyl corticoid, the (trimethylsilyl) protecting group is removed as is well known to those skilled in the art, see for example, U.S. Pat. No. 4,036,831.

The conjugate addition of a methylating agent, such as methyl Grignard, to a 16-unsaturated steroid to give the corresponding 16$\alpha$-methyl steroid is well known, see Organic Reactions in Steroid Chemistry, Vol. II, J. Fried and J. A. Edwards, p 75 and U.S. Pat. No. 3,072,686.

The 16-unsaturated corticoid (I) is reacted with a methylating agent followed by a silating agent to give the enol silane $\Delta^{17(20)}$-steroid (II). The methylating agent is selected from the group consisting of CH$_3$Cu, (CH$_3$)$_2$CuM or CH$_3$MgQ and a catalytic amount of a copper (cupric) salt. The preferred methylating agent is methyl Grignard, preferably methyl magnesium chloride. The copper salt can be a cuprous salt such as cuprous chloride, bromide, iodide or cyanide or a cupric salt such as cupric chloride, cupric acetate, cupric propionate or complexes thereof. Examples of copper complexes include, cuprous bromide dimethylsulfide, cuprous chloride tris-n-butylphosphine and cuprous acetylacetonate. The nature of the copper complex is not critical. Hundreds (or thousands) of copper complexes are known which are considered equivalent to those set forth above. Preferred is cupric acetate or propionate. Additional catalysts which are considered equivalent to those disclosed above are well known to those skilled in the art, see, for example, Alfa Catalog, 1983–1984, Morton Thiokol, Inc., Alpha Products, PO Box 299, 152 Andover Street, Danvers, Mass. 01923. Solvents suitable for the methylation reaction include those selected from the group consisting of THF, t-butylmethyl ether or dimethoxyethane. The reaction is performed in a range of from about $-50°$ to about 20°, preferably at about $-20°$. When TLC indicates that no starting material is left (indicating the probable formation of an enolate intermediate), the silating agent is added and the resulting product is the $\Delta^{17(20)}$ steroid (II). After the silylating agent is added the reaction temperature is kept in the range of about $-25°$ to about 25°, preferably about 0°.

In the present invention the enolate intermediate is trapped with the silylating agent which gives the $\Delta^{17(20)}$-20-(substituted silyl) product. Operable silylating agents include (R$_{20}$)$_3$-Si-E, bistrimethylsilylacetamide. It is preferred that the silating agent be of the formula (R$_{20}$)$_3$-Si-E, more preferably trimethylsilyl chloride. Additional silylating agents considered equivalent to those disclosed above are well known to those skilled in the art, see, for example Silicon Compounds, Petrarch Systems, Inc., Bartram Rd. Bristol, PA 19007. The trapping of the enolate intermediate to produce the $\Delta^{17(20)}$-20-(acetate) is known, see U.S. Pat. No. 4,031,080 and Organic Reactions in Steroid Chemistry, Vol. II, supra, p 76. These enol acylates are too unreactive to react selectively over A,B,C-ring functionality such as $\Delta^{9(11)}$. However, surprisingly and unexpectedly the $\Delta^{17(20)}$-20-(substituted silyl) derivative (II) is sufficiently reactive to react with electrophiles without affecting most of the other functionality in the A,B,C-rings.

The $\Delta^{17(20)}$-steroid (II) can be isolated if desired by means well known to those skilled in the art, see for example, Examples 1 and 8. However, since the desired product is the 16$\alpha$-methyl corticoid (V), it is not necessary and preferable not to isolate the $\Delta^{17(20)}$-steroid (II) but rather to continue the reaction, see Examples 3–5, 11 and 12.

The $\Delta^{17(20)}$-steroid (II) is reacted with a peracid to produce the 17$\alpha$,20-epoxide (III). While most peracids are operable, preferred peracids include m-chloroperbenzoic, perbenzoic, peracetic. The peracid-reaction conditions are well known to those skilled in the art.

The peracid reaction does not significantly affect the $\Delta^1$, $\Delta^4$, or $\Delta^{9(11)}$ functionalities in the remainder of the molecule, see Example 2. The solvent used during the methylation reaction producing the $\Delta^{17(20)}$-steroid (II) is removed and replaced by a non-polar solvent such as toluene, methylene chloride, ethyl acetate or t-butyl methyl ether. The inorganic salts remaining after the methylation reaction are removed by extraction. The peracid oxidation is performed in the temperature range of about $-10°$ to $25°$. When the reaction is complete, the excess peracid is destroyed by addition of an agent such as powdered sodium thiosulfate or sodium bisulfite. The 17α,20-epoxide (III) can be isolated if desired by means well known to those skilled in the art. However, since the desired product is the 16α-methyl corticoid (V), it is not necessary and preferable not to isolate the 17α,20-epoxide (III) but rather to continue the reaction in situ.

The 17α,20-epoxide (III) is transformed to the corresponding 16α-methyl corticoid (V) by acid or base hydrolysis. If base is used the 16α-methyl corticoid will be obtained as the 21-hydroxy compound ($R_{21}$ is a hydrogen atom). If acid is used the 16α-methyl corticoid will be the 21-ester ($R_{21}$ is —CO—$R_{21}'$). Suitable base hydrolyzing agents include hydroxide, carbonate, bicarbonate, alkoxide in alcohol at low temperature etc. It is preferred that the hydrolyzing agent be an acid. Suitable acids include mineral acids and other sufficiently strong acids such as p-TSA, sulfuric, hydrochloric, citric or acetic. The acid hydrolysis is sufficiently fast that the reaction is complete in about ½ hour at 20°–25°.

The 16α-methyl corticoids (V) are adrenocorticoid agents with glucocorticoid activity and are useful primarily for their anti-inflammatory effects as is well known to those skilled in the art. These include dexamethasone, flumethasone and paramethsone. One of the best known 16α-methyl corticoids is dexamethasone, see U.S. Pat. Nos. 3,375,261 and Re. 28,369 as well as the Physicians Desk Reference 1983, 37th Edition, p 1270–1283.

If the C-ring of the 16α-methyl corticoid (V) is $\Delta^{9(11)}$ or 9β,11β-epoxy, it is readily convertible to the pharmacologically active 9α-fluoro-11β-hydroxy C-ring by means well known to those skilled in the art.

DEFINITIONS

The definitions and explanations below are for the terms as used throughout the entire patent application including both the specification and the claims.

All temperatures are in degrees Centigrade.
TLC refers to thin-layer chromatography.
THF refers to tetrahydrofuran.
TMS refers to trimethylsilyl.
THP refers to tetrahydropyranyl.
EEE refers to (1-ethoxy) ethyl ether [—O—CH(CH$_3$)OCH$_2$CH$_3$].
p-TSA refers to p-toluenesulfonic acid monohydrate.
When solvent pairs are used, the ratio of solvents used are volume/volume (v/v).
DMSO refers to dimethylsulfoxide.
UV refers to ultraviolet spectroscopy.
NMR refers to nuclear (proton) magnetic resonance spectroscopy, chemical shifts are reported in ppm (δ) downfield from tetramethylsilane.
$[\alpha]_D^{25}$ refers to the angle of rotation of plane polarized light (specific optical rotation) at 25° with the sodium D line (5893A).
Dexamethasone refers to 9α-fluoro-11β,17α,21-trihydroxy-16α-methylpregna-1,4-diene-3,20-dione.
Paramethasone refers to 6α-fluoro-11β-17α-,21-trihydroxy-16α-methylpregna-1,4-diene-3,20-dione.
Flumethasone refers to 6α,9α-difluoro-11β-,17α-,21-trihydroxy-16α-methylpregna-1,4-diene-3,20-dione.
$R_3$ is alkyl of 1 thru 3 carbon atoms, a TMS, THP, or EEE group.
$R_3'$ is alkyl of 1 thru 5 carbon atoms or phenyl.
$R_6$ is a hydrogen or fluorine atom or methyl group.
$R_9$ is nothing, a hydrogen, fluorine or oxygen atom which makes the C ring
  (a) $\Delta^{9(11)}$ when $R_9$ is nothing and
  (b) 9β,11β-epoxide when $R_9$ and $R_{11}$ taken together are an oxygen atom.
$R_{11}$ is a hydrogen or oxygen atom, two hydrogen atoms, or α- or β-hydroxyl group or trimethylsilyl ether thereof which makes the C-ring
  (a) $\Delta^{9(11)}$ when $R_{11}$ is a hydrogen atom,
  (b) 9β,11β-epoxide when $R_9$ and $R_{11}$ taken together are an oxygen atom and ～ between $C_{11}$ and $R_{11}$ is a single bond, and
  (c) a ketone when $R_{11}$ is an oxygen atom and ⋯ between $C_{11}$ and $R_{11}$ is a double bond.
$R_{20}$ is alkyl of 1 thru 4 carbon atoms or phenyl, the $R_{20}$40 s can be the same or different.
$R_{21}$ is a hydrogen atom, —CO—$R_{21}'$ or —Si($R_{121}$)$_3$.
$R_{21}'$ is alkyl of 1 thru 4 carbon atoms or phenyl.
$R_{121}$ is alkyl of 1 thru 4 carbon atoms or phenyl, the $R_{121}'$s can be the same or different.
～ indicates that the attached group can be in either the α or β configuration.
⋯ is a single or double bond.
When the term "alkyl of― through― carbon atoms" is used, it means and includes isomers thereof where such exist.
X is a hydrogen atom or nothing; when X is nothing the ⋯ at $C_3$ is a double bond and when X is a hydrogen atom the ⋯ at $C_3$ is a single bond.
M is a lithium or magnesium ion.
Q is a chlorine, bromine or iodine atom.
E is a chlorine, bromine or iodine atom or —NRαRβ.
Rα is alkyl of 1 thru 5 carbon atoms or phenyl and may be connected or cyclized with Rβ in a ring with or without an oxygen or additional nitrogen atom.
Rβ is alkyl of 1 thru 5 carbon atoms or phenyl and may be connected or cyclized with Rα in a ring with or without an oxygen or additional nitrogen atom.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLE 1

20,21-Dihydroxy-16α-methylpregna-1,4,9(11),17(20)-tetraen-3-one 20-trimethyl silyl ether 21-acetate (IIB)

Methyl magnesium chloride in THF (2M, 4.5 ml) is added over a period of 2.5 hr to a mixture of 21-hydroxypregna-1,4,9(11),16-tetraene-3,20-dione 21-acetate (IB, U.S. Pat. No. 4,031,080, 2.0 g), THF (27 ml) and cupric acetate monohydrate (60 mg) previously cooled to −52°. The reaction temperature is kept at less than −40° during the Grignard addition. Following the Grignard addition, TLC indicated no starting material is left and the reaction mixture is quenched with trimethylsilyl chloride (1.1 ml). The reaction temperature is then slowly permitted to rise to 4° over a period of 3 hr at which time TLC indicated the reaction is complete. Toluene (15 ml) is added and the THF removed under reduced pressure maintaining the reaction medium at 10°–15°. The reaction mixture is first extracted with a pH 7 buffer, then 4 times with buffer (1 ml) and water (9 ml) and lastly with water. The layers are separated and the organic layer is dried over sodium sulfate at less than 0° for 48 hr. The toluene solution is divided into 35 two-ml portions, one of which is concentrated under reduced pressure to give the title compound.

EXAMPLE 2

17α,21-Dihydroxy-16α-methylpregna-1,4,9(11)-triene-3,20-dione 21-acetate (VB)

m-Chloroperbenzoic acid (0.556 g) is added dropwise to 20,21-dihydroxy-16α-methylpregna-1,4,9(11),17(20)-tetraen-3-one 20-trimethylsilyl ether 21-acetate (IIB, Example 1, one 35 ml aliquot) over about a 3 hr period keeping the bath temperature in the range of about −9° to about 0°. The reaction is quenched with sodium bisulfite (1M, 2.8 ml). Water is added and the phases are separated. The organic phase is washed with water, buffer and water, dried over sodium sulfate and concentrated to a solid. The solid is dissolved in ethyl acetate/hexane (5 ml) and crystals formed overnight. The filtrate is concentrated to a solid which is dissolved in methanol and cooled to 0°. The mixture is filtered, and the crystals washed with cold methanol.

TLC shows some 21-hydroxy compound (V) is present. Acetic anhydride (0.1 ml) and pyridine (0.4 ml) is added and the mixture stirred overnight. The mixture is worked up as is well known to those skilled in the art to give a solid which is crystallized from 40% aqueous methanol to give the title compound.

EXAMPLE 3

9β,11β-Epoxy-17α,21-dihydroxy-16α-methylpregna-1,4-diene-3,20-dione 21-acetate (VB)

A mixture of 9β,11β-epoxy-21-hydroxypregna-1,4,16-triene-3,20-dione 21-acetate (IB, Example 7, 3.824 g) and cupric acetate monohydrate (200 mg) and anhydrous THF (70 ml) at −15° is treated with methyl magnesium chloride (2.2M, 8.2 ml) added dropwise over 1 hour. After 10 minutes of stirring at −15° trimethylchlorosilane (1.64 ml) is added. The mixture is immediately warmed to 20°, stirred for 1 hour at which time TLC shows enol ether (II) formation to be complete. The mixture is added to toluene (100 ml) and this is washed with monobasic phosphate buffer (pH 4.25, 50 ml). The organic layer is separated and washed with water (2×50 ml) and each aqueous layer is back-extracted with toluene (15 ml). The organic phases are combined and concentrated at 55° under reduced pressure to a residue.

Toluene (30 ml) at 0° is added and the mixture treated with peroxyacetic acid (34.5%, 2.91 ml) containing sodium acetate (164 mg). The stirred mixture is warmed to 20° and after 10 minutes TLC indicates the peroxidation is complete. The excess peracid is destroyed by addition of powdered sodium thiosulfate (2.5 g) slurried in methanol (10 ml). Hydrochloric acid (6N, 3.0 ml) is added and the hydrolysis is complete in about 10 minutes. The mixture is added to toluene (75 ml) and the organic phase washed with water (2×50 ml), sodium carbonate solution (5%, 40 ml) and finally with water (50 ml). Each aqueous phase is back-extracted sequentially with toluene (20 ml). The organic phases are combined and concentrated under reduced pressure to a crystalline residue which is dissolved in hot ethyl acetate and filtered to remove traces of inorganics. Ethyl acetate (about 5 ml) is used for rinse. The combined volumes of the filtrate and rinse are reduced to about 10 ml. The solids formed and after about 1 hour hexane (4 ml) is added. After standing at 30°–40° for 2 hours the slurry is cooled to 20°, and the solids collected by vacuum filtration. The solids are washed with cold ethyl acetate:hexane, 1:1 (3 ml), and dried under reduced pressure at 50°–60° for 3 hours to give the title compound, mp 180°–186° with softening at about 135°; NMR (CDCl₃) 0.89, 0.92, 1.43, 3.18 and 4.83 δ.

EXAMPLE 4

9β,11β-Epoxy-6α-fluoro-17α,21-dihydroxy-16α-methyl pregna-1,4-diene-3,20-dione (VB)

A mixture of 9β,11β-epoxy-6α-fluoro-21-hydroxy-1,4,16-triene-3,20-dione 21-acetate (IB, U.S. Pat. No. 3,210,341, 8.009 g) cupric acetate monohydrate (400 mg) and tri-n-butyl phosphine (1 ml) in anhydrous THF (120 ml) at −11° is treated with methyl magnesium chloride (1.95M, 26.5 ml) added dropwise over 1 hour. Trimethylchlorosilane (4 ml) at −8° is then added. The mixture is immediately allowed to warm to 14° and after 20 minutes TLC indicates the reaction is complete. The mixture is added to ethyl acetate (300 ml) and washed with ammonium hydroxide:saturated ammonium chloride, 1:1 (2×75 ml). Each aqueous extract is sequentially washed with the same portion of ethyl acetate (210 ml). The combined organic phases are then concentrated at 45° under reduced pressure to an oil. The oil is taken up in methylene chloride (120 ml) at −10° and treated with m-chloroperoxybenzoic acid (85%, 6.092 g) and after 1.5 hours TLC indicates the epoxidation is complete. The mixture is vacuum distilled to replace the solvent with methanol (100 ml) and then the mixture is treated with saturated sodium carbonate (20 ml). After stirring 16 hours at 20°–25° and 5.25 hours at 55° TLC showed the hydrolysis is complete. After cooling to 20°–25° water (100 ml) is added and the pH adjusted to 7.5 using acetic acid (0.2 ml). Water (160 ml) is then added portion-wise at 5°. The solids that formed are collected by filtration, washed with 0° methanol in water (25:75, 50 ml) and dried under reduced pressure at about 84° over 16 hours to give the title compound, mp 241°–241.5°; [α]$_D^{25}$ = +45.7° (DMSO); UV λ$_{max}$=245 nm (ε=15,300); NMR (CDCl₃/DMSO-d₆) 0.82, 0.82, 1.40, 3.30, 4.30 and 5.52 δ.

EXAMPLE 5

17α,21-Dihydroxy-16α-methylpregna-4,9(11)-diene-3,20-dione 21-acetate (VA)

Methyl magnesium chloride in THF (2M, 6.2 ml) is added to a mixture of 21-hydroxypregna-4,9(11),16-triene-3,20-dione 21-acetate (IA, U.S. Pat. No. 4,216,159, 3.68 g) and cupric acetate monohydrate (200 mg) in dry THF (100 ml) at −50° over a period of 17 minutes. The mixture is stirred at −45° to −50° for 20 minutes and then treated with trimethylchlorosilane (1.9 ml) and allowed to warm to 20°–25°. After 1.5 hours at 20°–25° TLC indicates the enol silyl ether formation is complete. The reaction mixture is added to ethyl acetate (150 ml) and this mixture is washed with cold sulfuric acid (5%, 200 ml), the layers are separated, the aqueous layer is back-extracted with ethyl acetate (25 ml). The original organic layer is washed with cold water (2×150 ml) which in turn was back-extracted with additional ethyl acetate. The organic layers phases are combined and concentrated under reduced pressure to about 100 ml.

m-Chloroperoxybenzoic acid (85%, 1.72 g) is added and the mixture stirred 1 hour at −15° following which another 300 mg of peracid is added and the mixture stirred at 20° overnight. The excess peracid is destroyed by treatment with sodium bisulfite solution (10%, 20 ml). The mixture is stirred for 20 minutes and then diluted with toluene (200 ml). The mixture is then washed with sulfuric acid (5%, 100 ml) and water (2×100 ml). After concentration to dryness under reduced pressure the residue is dissolved in methanol (100 ml) and treated with hydrochloric acid (3N, 0.5 ml). The mixture is again concentrated to a higher boiling residue which is taken up in toluene (200 ml). This mixture is washed with saturated sodium carbonate (100 ml) to remove the m-chlorobenzoic acid. Finally the organic layers are washed with water (2×100 ml) and concentrated as above. The residue dissolved in hot methanol (20 ml) for crystallization. After cooling to 0° for several hours a solid is obtained which is collected by vacuum filtration. The product is washed with cold methanol and dried at 20° to give the title compound; NMR 0.73, 0.93, 1.33 and 4.98 δ.

EXAMPLE 6

9β,11β-Epoxy-21-hydroxypregna-4,16-diene-3,20-dione 21-acetate (IA)

Following the general procedure of U.S. Pat. No. 3,876,633 and making non-critical variations, but starting with 21-hydroxypregna-4,9(11),16-triene-3,20-dione 21 acetate (U.S. Pat. No. 2,773,080), the title compound is obtained, mp 129°–130.5°.

EXAMPLE 7

9β,11β-Epoxy-21-hydroxypregna-1,4,16-triene-3,20-dione 21-acetate (IB)

Following the general procedure of U.S. Pat. No. 3,876,633 and making non-critical variations, but starting with 21-hydroxypregna-1,4,9(11),16-tetraene-3,20-dione 21-acetate (U.S. Pat. No. 2,864,834) the title compound is obtained, mp 163.5°–165°.

EXAMPLE 8

9β,11β-Epoxy-17α,21-dihydroxy-16α-methylpregna-1,4-diene-3,20-dione (VB)

A mixture of 9β,11β-epoxy-21-hydroxypregna-1,4,16-triene-3,20-dione 21-acetate (IB, Example 7, 7.650 g) and cupric acetate monohydrate (400 mg) in dry THF (130 ml) is stirred under nitrogen. The temperature is adjusted to −20° and 1,1,3,3-tetramethylurea (5.0 ml) is added. Methyl magnesium chloride (2M, 16.6 ml) is added dropwise over 50 min at −17° to −19°. TLC indicates the Grignard reaction is complete. The mixture is stirred for 40 min at −19°, following which the magnesium enolate is quenched with trimethylchlorosilane (3.28 ml). The temperature rises to 25° during the 1 hr stir period. TLC shows this reaction is complete. The mixture is added to toluene (150 ml) and monobasic potassium phosphate buffer (pH 4.3, 10%, 50 ml). The aqueous layer is extracted with toluene (25 ml) and then is discarded. The two organic layers are washed sequentially with water (2×50 ml), then combined and concentrated to a high boiling residue.

The residue containing the Δ$^{17(20)}$-20-enol silane is dissolved in toluene (60 ml). After cooling to −5°, 5.9 ml of 4.4M peroxyacetic acid containing sodium acetate (91 mg) is added and the mixture stirred for 80 min. TLC shows the epoxidation is complete. The excess peracid is destroyed with aqueous sodium bisulfite (1.5M, 10 ml) at about 0°. After stirring 5 min the mixture is added to toluene (40 ml) and water (55 ml). The layers are separated and the aqueous phase is extracted with toluene (20 ml) and then discarded. The two organic layers are washed sequentially with saturated sodium bicarbonate (20 ml) and water (35 ml). The combined organic layers are filtered thru cotton and concentrated to a high boiling residue of the 17α,20-epoxide.

The epoxide is taken up in methanol (60 ml) and treated with p-TSA (5 mg) at 21°. After 6 min TLC indicates the epoxide is opened and the 16α-methyl corticoid has formed (as the 21-acetate). A saturated sodium carbonate solution (1.9 ml) is added and the slurry stirred at 55° for 45 min. TLC indicates the hydrolysis is complete. Water (30 ml) is added and the slurry is stored at 0° overnight. The solids are collected by filtration, washed with methanol/water (1/1) and dried under reduced pressure at 70° for 4.5 hr to give the title compound, mp 238°–239.5°.

EXAMPLE 9

9β,11β-Epoxy-20,21-dihydroxy-16α-methylpregna-1,4,17(20)-trien-3-one-20-trimethylsilyl ether 21-acetate (IIB)

Following the general procedure of Example 1 and making noncritical variations but starting with 9β,11β-epoxy-21-hydroxy-1,4,16-triene-3,20-dione 21-acetate (IB, Example 7) the title compound is obtained.

EXAMPLE 10

9α-Fluoro-11β,21-dihydroxypregna-1,4,16-triene-3,20-dione 21-acetate (IB)

9β,11β-Epoxy-21-hydroxypregna-1,4,16-triene-3,20-dione 21-acetate (IB, Example 7, 15.3 g) is added to a stirred mixture of aqueous hydrogen fluoride (72%, 55 ml) and methylene chloride (15 ml) at −25° in a 200 ml monel reactor fitted with a mechanical agitator. About 30 ml of methylene chloride is used as a rinse. The mixture is stirred at −22° for 2.5 hr and then at −4° to −11° for 4.0 hr. The mixture is treated with THF (35 ml) at −10° and then quenched carefully by slow addition of a mixture of THF (60 ml), aqueous potassium carbonate (47%, 202 ml) and water (100 ml). After stirring 20 min the mixture is added to toluene (400 ml) and water (400 ml). the phases are separated and the organic layer is washed with water (3×150 ml), dried by filtration thru cotton and concentration to about 150 ml. Methylene chloride (about 150 ml) and magnesol (0.90 g) is added to the mixture. After 15 min the magnesol is removed by filtration. The filtrate is again concentrated to 150 ml and then cooled to 0°. Solids form after stirring at 0° for 3 hr and the product is collected by filtration. The solids are washed with toluene (2×25 ml) and dried at 60° for 3 hr under vacuum to give the title compound, mp=223°-225°; NMR (CDCl₃) 1.27, 1.59, 4.29, 4.93 and 6.77δ.

EXAMPLE 11

9α-FLuoro-11β,20,21-trihydroxy-16α-methylpregna-1,4,17(20)-triene-3-one 11,20-bis(trimethylsilyl)ether 21-acetate (IIB)

A solution of copper (II) propionate (151 mg) in dry THF (60 ml) is cooled to −30° and then treated with methyl magnesium chloride (2M, about 1 ml) in order to reduce the copper to copper (I). 9α-Fluoro-11β,21-dihydroxypregna-1,4,16-triene-3,20-dione 21-acetate (IB, Example 10, 2.025 g) is added to the copper mixture. The temperature is adjusted to −33° and the above Grignard reagent (3.0 ml) is added. A slurry forms which is dissolved when treated with trimethylsilyl chloride (1.50 ml). After stirring 1 hr at −40° another 7.4 ml of the Grignard reagent is added portionwise over 50 min. The mixture is stirred another 2 hr and the temperature is allowed to rise to −26°. Then trimethylsilyl chloride (2.0 ml) is added over 1.25 hr at −15°. TLC indicates formation of the $\Delta^{17(20)}$-enol ether is not complete after another 0.5 hr at −15°. Grignard reagent (3.0 ml) is added at −35°. After 20 min the mixture is added to toluene (150 ml). This mixture is washed with 150 ml of water containing 20 ml of 5% phosphate buffer (pH 6.5). The phases are separated and the organic layer is washed with water (2×75 ml) and then dried by filtration thru cotton to give the title compound in solution.

EXAMPLE 12

17α,20-Epoxy-9α-fluoro-11β,20,21-trihydroxy-16α-methylpregna-1,4-dien-3-one 11,20-bis(trimethylsilyl)ether 21-acetate (IIIB)

The above filtrate (Example 11) is concentrated to about 50 ml and after cooling this mixture to −17°, peroxyacetic acid (4.44M, 3.37 ml) containing sodium acetate (67 mg) is added. The mixture is stirred for 4 hr while the temperature is allowed to rise to 7°. The mixture is diluted with toluene and then washed with water (75 ml), dilute sodium sulfite and finally with water (75 ml). Each aqueous wash is back-extracted with toluene (50 ml). The organic phases are combined, and concentrated under vacuum distillation to give a higher boiling residue of crude 17(20)-epoxide-20-trimethylsilyl ether (III).

EXAMPLE 13

9α-Fluoro-11β,17α,21-trihydroxy-16α-methylpregna-1,4-diene-3,20-dione 21-acetate (VB)

The residue (Example 12) is dissolved in methanol (30 ml) and allowed to stand at room temperature. After 0.75 hr the mixture is concentrated to 15 ml and water (10 ml) is added. The mixture is filtered to remove traces of insoluble material. The filtrate is diluted with more water and a waxy solid is collected by decantation. The solid is dried and then recrystallized from acetone/hexane (¼, 35 ml). The solids are collected by filtration, washed with acetone/hexane (¼, 5 ml) and dried at room temperature to give the title compound. A pure sample of the title compound is obtained by column chromatography followed by crystallizaion from acetone/hexane (1/1), mp=227°-229°; NMR (CDCl₃) 0.89, 1.03, 1.57, 4.29 and 4.93δ.

EXAMPLE 14

17α,20-Epoxy-20,21-dihydroxy-16α-methylpregna-1,4,9(11)-trien-3-one 20-trimethylsilyl ether 21-acetate (IIIB)

Following the general procedure of Example 12 and making non-critical variations, but starting with 20,21-dihydroxy-16α-methylpregna-1,4,9(11),17(20)-tetraen-3-one 20-trimethylsilyl ether 21-acetate (IIB, Example 1) the title compound is obtained.

EXAMPLE 15

9β,11β,17α,20-Diepoxy-20,21-dihydroxy-16α-methylpregna-1,4-dien-3-one 20-trimethylsilyl ether 21-acetate (IIIB)

Following the general procedure of Example 12 and making non-critical variations, but starting with 9β,11β-epoxy-20,21-dihydroxy-16α-methylpregna-1,4,17(20)-trien-3-one 20-trimethylsilyl ether 21-acetate (IIB, Example 9) the title compound is obtained.

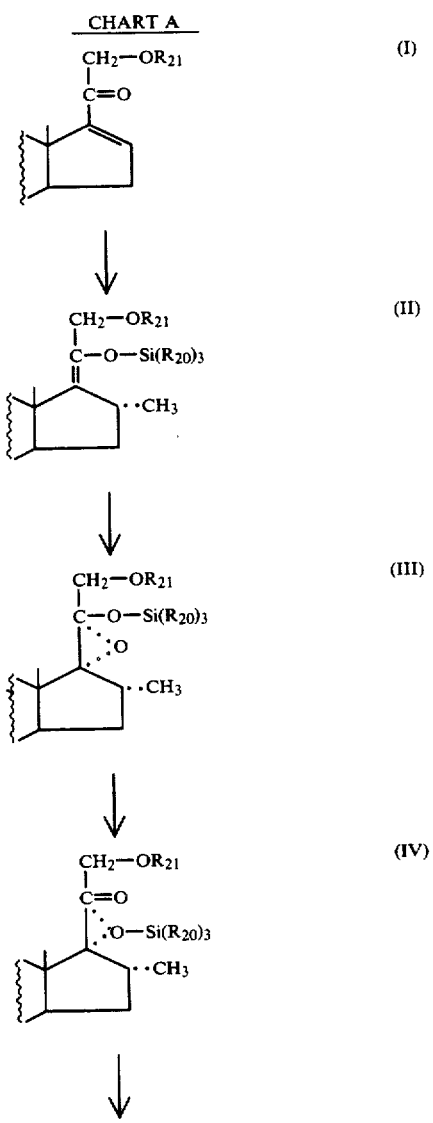

CHART A

-continued
CHART A

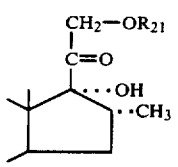

CHART B

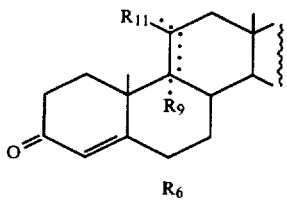

(Ca)
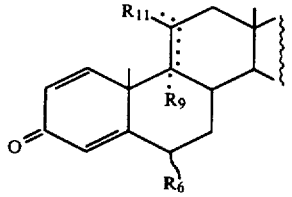

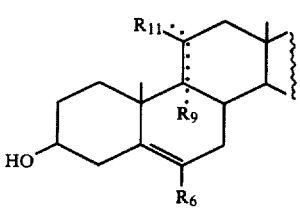

CHART C

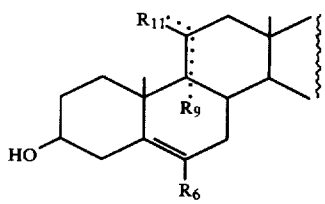

(Cb)
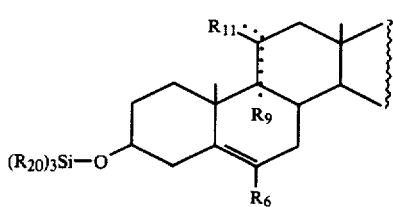

-continued
CHART C (V) 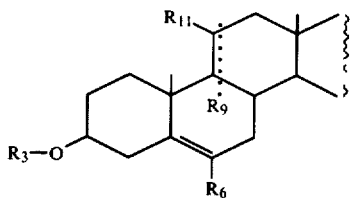 (Cc)

(A) 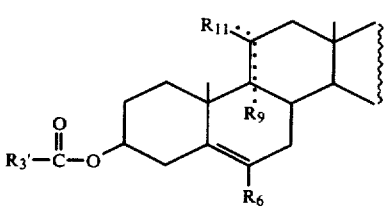 (Cd)

ENUMERATED EMBODIMENTS (1) A $\Delta^{17(20)}$-corticoid of the formula (C) 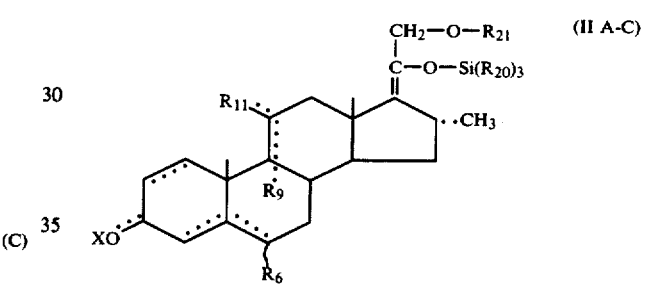 (II A-C)

and the C$_3$ protected forms of the 3$\beta$-hydroxy-$\Delta^5$-(C) A-ring where R$_6$ is a hydrogen or fluorine atom or methyl group;
R$_9$ is nothing, a hydrogen, fluorine or oxygen atom which makes the C ring
  (a) $\Delta^{9(11)}$ when R$_9$ is nothing and
  (b) 9$\beta$,11$\beta$-epoxide when R$_9$ and R$_{11}$ taken together are an oxygen atom;
R$_{11}$ is a hydrogen or oxygen atom, two hydrogen atoms, or $\alpha$- or $\beta$-hydroxy group or trimethylsilyl ether thereof which makes the C-ring
  (a) $\Delta^{9(11)}$ when R$_{11}$ is a hydrogen atom,
  (b) 9$\beta$,11$\beta$-epoxide when R$_9$ and R$_{11}$ taken together are an oxygen atom and ⋯ between C$_{11}$ and R$_{11}$ is a single bond, and
  (c) a ketone when R$_{11}$ is an oxygen atom and ⋯ between C$_{11}$ and R$_{11}$ is a double bond;
R$_{20}$ is alkyl of 1 thru 4 carbon atoms or phenyl, the R$_{20}$'s can be the same or different;
R$_{21}$ is a hydrogen atom, —CO—R$_{21}$' or —Si(R$_{121}$)$_3$;
R$_{21}$' is alkyl of 1 thru 4 carbon atoms or phenyl;
R$_{121}$ is alkyl of 1 thru 4 carbon atoms or phenyl, the R$_{121}$'s can be the same or different;
~ indicates that the attached group can be in either the $\alpha$ or $\beta$ configuration;
⋯ is a single or double bond; and
X is a hydrogen atom or nothing; when X is nothing the ___ at C$_3$ is a double bond and when X is a hydrogen atom the ⋯ at C$_3$ is a single bond.

(2) A $\Delta^{17(20)}$-corticoid according to Enumerated Embodiment 1 where the $\Delta^{17(20)}$-corticoid (II A-C) is a $\Delta^4$-3-keto (A) or $\Delta^{1,4}$-3-keto (B) steroid.

(3) A $\Delta^{17(20)}$-corticoid according to Enumerated Embodiment 1 where the $\Delta^{17(20)}$-corticoid (II A-C) is a 3$\beta$-hydroxy-$\Delta^5$ (C) steroid in the free form

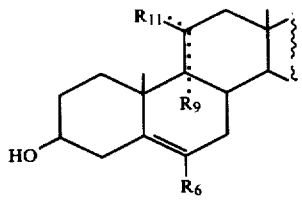
(Ca)

or C$_3$ protected form selected from the group consisting of

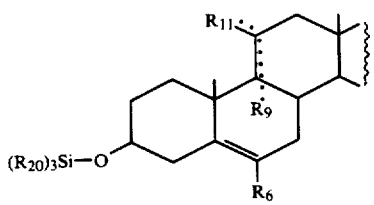
(Cb)

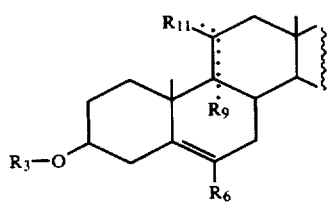
(Cc)

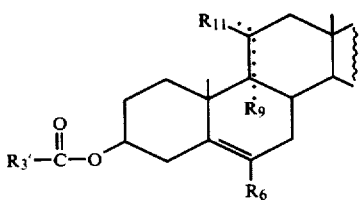
(Cd)

where
R$_3$ is alkyl of 1 thru 3 carbon atoms, a TMS, THP or EEE group;
R$_3$' is alkyl of 1 thru 5 carbon atoms or phenyl;
TMS refers to trimethylsilyl;
THP refers to tetrahydropyranyl;
EEE refers to (1-ethoxy)ethyl ether[—O—CH(CH$_3$)OCH$_2$CH$_3$];
where R$_6$, R$_9$, R$_{11}$, R$_{20}$ and ⁓ are defined in Enumerated Embodiment 1.

(4) A $\Delta^{17(20)}$-corticoid according to Enumerated Embodiment 1 where R$_6$ is a hydrogen atom.

(5) A $\Delta^{17(20)}$-corticoid according to Enumerated Embodiment 1 where R$_9$ is nothing or an oxygen atom and where R$_{11}$ is a hydrogen atom or an oxygen atom making the C-ring $\Delta^{9(11)}$ or a 9$\beta$,11$\beta$-epoxide.

(6) A $\Delta^{17(20)}$-corticoid according to Enumerated Embodiment 1 where R$_{20}$ is selected from the group consisting of methyl, isopropyl, t-butyl or phenyl.

(7) A $\Delta^{17(20)}$-corticoid according to Enumerated Embodiment 1 where R$_{20}$ is methyl or phenyl.

(8) A $\Delta^{17(20)}$-corticoid according to Enumerated Embodiment 1 where R$_{21}$ is —CO—R$_{21}$' and R$_{21}$' is selected from the group consisting of methyl, ethyl or phenyl.

(9) A $\Delta^{17(20)}$-corticoid according to Enumerated Embodiment 1 which is selected from the group consisting of 20,21-dihydroxy-16$\alpha$-methylpregna-1,4,9(11),17(20)-tetraen-3-one 20-trimethylsilyl ether 21-acetate, 9$\beta$,11$\beta$-epoxy-20,21-dihydroxy-16$\alpha$-methylpregna-1,4,17(20)-triene-3-one 20-trimethylsilyl ether 21-acetate and 9$\alpha$-fluoro-11$\beta$,20,21-trihydroxy-16$\alpha$-methylpregna, 1,4,17(20)-triene-3-one 11,20-bis(trimethylsilyl)ether 21-acetate.

(10) A 17$\alpha$,20-epoxy steroid of the formula

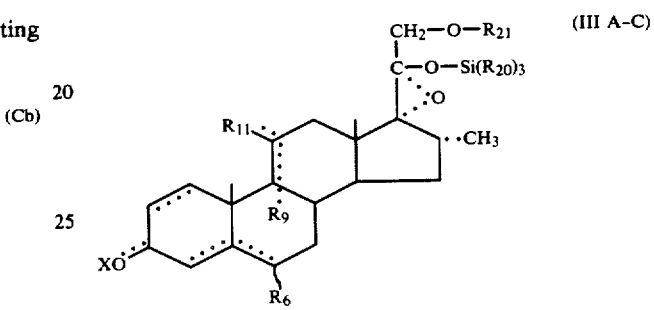
(III A-C)

and the C$_3$-protected forms of the 3$\beta$-hydroxy-$\Delta^5$ (C) A-ring where
R$_6$ is a hydrogen or fluorine atom or methyl group;
R$_9$ is nothing, a hydrogen, fluorine or oxygen atom which makes the C ring
  (a) $\Delta^{9(11)}$ when R$_9$ is nothing and
  (b) 9$\beta$,11$\beta$-epoxide when R$_9$ and R$_{11}$ taken together are an oxygen atom.

R$_{11}$ is a hydrogen or oxygen atom, two hydrogen atoms, or $\alpha$- or $\beta$-hydroxyl group or trimethylsilyl ether thereof which makes the C-ring
  (a) $\Delta^{9(11)}$ when R$_{11}$ is a hydrogen atom,
  (b) 9$\beta$,11$\beta$-epoxide when R$_9$ and R$_{11}$ taken together are an oxygen atom and ⁓ between C$_{11}$ and R$_{11}$ is a single bond, and
  (c) a ketone when R$_{11}$ is an oxygen atom and between C$_{11}$ and R$_{11}$ is a double bond;

R$_{20}$ is alkyl of 1 thru 4 carbon atoms or phenyl, the R$_{20}$'s can be the same or different;
R$_{21}$ is a hydrogen atom, —CO—R$_{21}$' or —Si(R$_{121}$)$_3$;
R$_{21}$' is alkyl of 1 thru 4 carbon atoms or phenyl;
R$_{121}$ is alkyl of 1 thru 4 carbon atoms or phenyl, the R$_{121}$'s can be the same or different;
⁓ indicates that the attached group can be in either the $\alpha$ or $\beta$ configuration;
⋯ is a single or double bond;
X is a hydrogen atom or nothing; when X is nothing the ⋯ at C$_3$ is a double bond and when X is a hydrogen atom the ⋯ at C$_3$ is a single bond.

(11) A 17$\alpha$,20-epoxy steroid according to Enumerated Embodiment 10 where the 17$\alpha$,20-epoxy steroid (III A-C) is a $\Delta^4$-3-keto (A) or $\Delta^{1,4}$-3-keto (B) steroid.

(12) A 17$\alpha$-,20-epoxy steroid according to Enumerated Embodiment 9 where the 17$\alpha$,20-epoxy steroid (IIIA-C) is a 3$\beta$-hydroxy $\Delta^5$ (C)-steroid in the free form or C3 protected form selected from the group consisting of

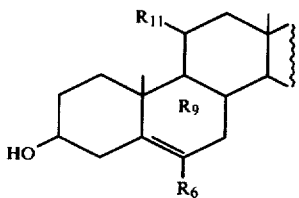

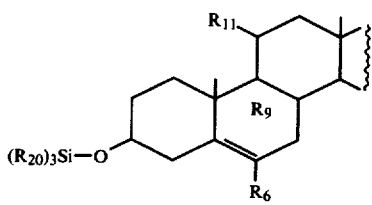

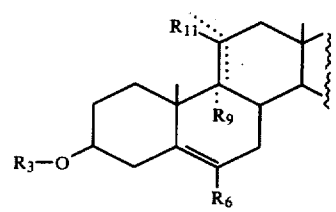

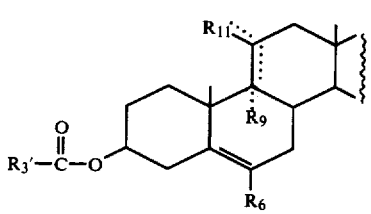

where
R3 is alkyl of 1 thru 3 carbon atoms, a TMS, THP or EEE group;
R3' is alkyl of 1 thru 5 carbon or phenyl;
TMS refers to trimethylsilyl;
THP refers to tetrahydropyranyl;
EEE refers to (1-ethoxy)ethyl ether[—O—CH(CH3)OCH2CH3];
where R6, R9, R11, R20 are defined in Enumerated Embodiment 10.

(13) A 17α,20-epoxy steroid according to Enumerated Embodiment 10 where R6 is a hydrogen atom.

(14) A 17α,20-epoxy steroid according to Enumerated Embodiment 10 where R9 is nothing or an oxygen atom and where R11 is a hydrogen atom or an oxygen atom making the C-ring $\Delta^{9(11)}$ or a 9β,11β-epoxide.

(15) A 17α,20-epoxy steroid according to Enumerated Embodiment 10 where R20 is selected from the group consisting of methyl, isopropyl, t-butyl or phenyl.

(16) A 17α,20-epoxy steroid according to Enumerated Embodiment 10 where R20 is methyl or phenyl.

(17) A 17α,20-epoxy steroid according to Enumerated Embodiment 10 where R21 is —CO—R21' and R21' is selected from the group consisting of methyl, ethyl or phenyl.

(18) A 17α-silyl ether of the formula

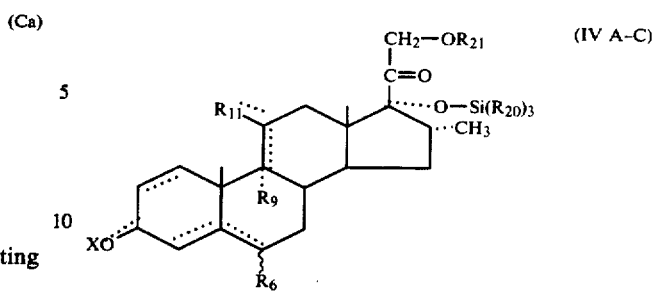

and the C3 protected forms of the 3β-hydroxy-$\Delta^5$-(C) A-ring where
R6 is a hydrogen or fluorine atom or methyl group;
R9 is nothing, a hydrogen, fluorine or oxygen atom which makes the C ring
 (a) $\Delta^{9(11)}$ when R9 is nothing and
 (b) 9β,11β-epoxide when R9 and R11 taken together are an oxygen atom.

R11 is a hydrogen or oxygen atom, two hydrogen atoms, or α- or β-hydroxyl group or trimethylsilyl ether thereof which makes the C-ring
 (a) $\Delta^{9(11)}$ when R11 is a hydrogen atom,
 (b) 9β,11β-epoxide when R9 and R11 taken together are an oxygen atom and ⋯ between C11 and R11 is a single bond, and
 (c) a ketone when R11 is an oxygen atom and ⋯ between C11 and R11 is a double bond;

R20 is alkyl of 1 thru 4 carbon atoms or phenyl, the R20's can be the same or different;
R21 is a hydrogen atom, —CO—R21' or —Si(R121)3;
R21' is alkyl of 1 thru 4 carbon atoms or phenyl;
R121 is alkyl of 1 thru 4 carbon atoms or phenyl, the R121's can be the same or different;

~ indicates that the attached group can be in either the α or β configuration;
⋯ is a single or double bond;
X is a hydrogen atom or nothing; when X is nothing the ⋯ at C3 is a double bond and when X is a hydrogen atom the ⋯ at C3 is a single bond.

(19) A 17α-silyl ether according to Enumerated Embodiment 18 where the 17α-silyl ether (IV A-C) is a $\Delta^4$-3-keto (A) or $\Delta^{1,4}$-3-keto (B) steroid.

(20) A 17α-silyl ether according to Enumerated Embodiment 18 where the 17α-silyl ether (IV A-C) is a 3β-hydroxy-$\Delta^5$ (C) steroid in the free form

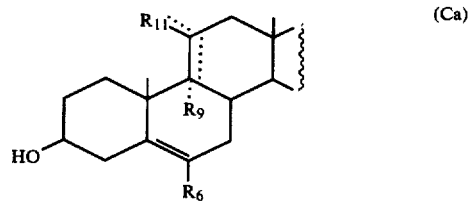

or C3 protected form selected from the group consisting of

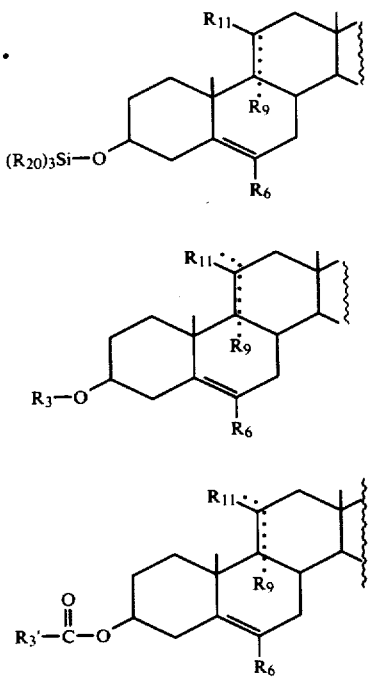

where
$R_3$ is alkyl of 1 thru 3 carbon atoms, a TMS, THP or EEE group;

$R_3'$ is alkyl of 1 thru 5 carbon or phenyl;

TMS refers to trimethylsilyl;

THP refers to tetrahydropyranyl;

EEE refers to (1-ethoxy) ether ethyl [—O—CH(CH$_3$)OCH$_2$CH$_3$];

where $R_6$, $R_9$, $R_{11}$, $R_{20}$ are defined in Enumerated Embodiment 18.

(21) A 17α-silyl ether according to Enumerated Embodiment 18 where $R_6$ is a hydrogen atom.

(22) A 17α-silyl ether according to Enumerated Embodiment 18 where $R_9$ is nothing or an oxygen atom and where $R_{11}$ is a hydrogen atom or an oxygen atom making the C-ring $\Delta^{9(11)}$ or a 9β,11β-epoxide.

(23) A 17α-silyl ether according to Enumerated Embodiment 18 where $R_{20}$ is selected from the group consisting of methyl, iospropyl, t-butyl or phenyl.

(24) A 17α-silyl ether according to Enumerated Embodiment 18 where $R_{20}$ is methyl or phenyl.

(25) A 17α-silyl ether according to Enumerated Embodiment 18 where $R_{21}$ is —CO—R$_{21}'$ and R$_{21}'$ is selected from the group consisting of methyl, ethyl or phenyl.

(26) 9β,11β-Epoxy-21-hydroxypregna-4,16-diene-3,20-dione 21-acetate.

(27) 9β,11β-Epoxy-21-hydroxypregna-1,4,16-triene-3,20-dione 21-acetate.

(28) A process for the preparation of a $\Delta^{17(20)}$-steroid of the formula

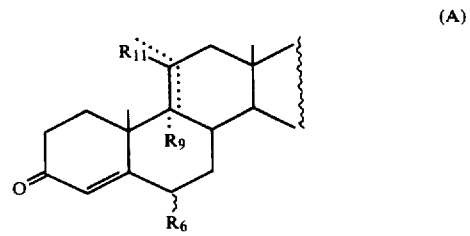

which comprises starting with a 16-unsaturated corticoid of the formula

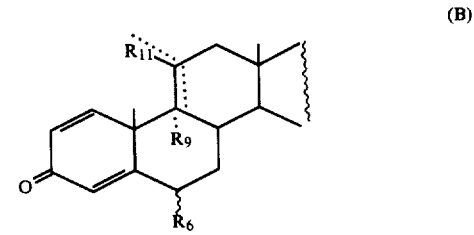

and (1) contacting the 16-unsaturated corticoid (I) with a methylating agent in the presence of a copper catalyst and (2) contacting the product of step (1) with a silylating agent where $R_{20}$ is alkyl of 1 thru 4 carbon atoms or phenyl, the $R_{20}$'s can be the same or different;

$R_{21}$ is a hydrogen atom, —CO—R$_{21}'$ or —Si(R$_{121}$)$_3$;

$R_{21}'$ is alkyl of 1 thru 4 carbon atoms or phenyl;

$R_{121}$ is alkyl of 1 thru 4 carbon atoms or phenyl, the $R_{121}$'s can be the same or different.

(29) A process according to Enumerated Embodiment 28 where the 16-unsaturated corticoid (I) is selected from the group consisting of $\Delta^4$-3-keto steroids (A)

$\Delta^{1,4}$-3-keto steroids (B)

and 3β-hydroxy-$\Delta^5$ steroids

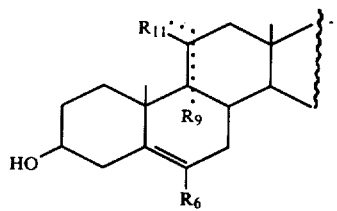

and the C₃ protected forms of the 3β-hydroxy-Δ⁵ (C) steroid

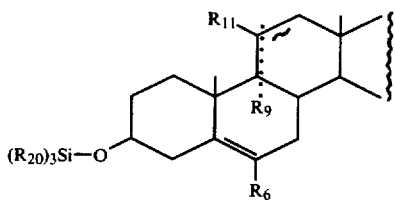

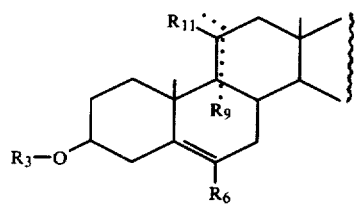

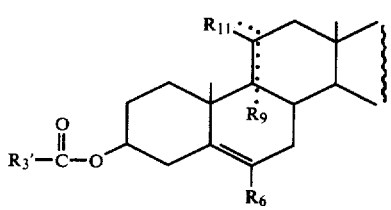

where $R_3$ is alkyl of 1 thru 3 carbon atoms, a TMS, THP, or EEE group;

$R_3'$ is alkyl of 1 thru 5 carbon atoms or phenyl;

$R_6$ is a hydrogen or fluorine atom or methyl group;

$R_9$ is nothing, a hydrogen, fluorine or oxygen atom which makes the C ring (a) $\Delta^{9(11)}$ when $R_9$ is nothing and (b) 9β,11β-epoxide when $R_9$ and $R_{11}$ taken together are an oxygen atom;

$R_{11}$ is a hydrogen or oxygen atom, two hydrogen atoms, or α- or β-hydroxyl group or trimethylsilyl ether thereof which makes the C-ring (a) $\Delta^{9(11)}$ when $R_{11}$ is a hydrogen atom, (b) 9β,11β-epoxide when $R_9$ and $R_{11}$ taken together are an oxygen atom and ⎯⎯⎯ between $C_{11}$ and $R_{11}$ is a single bond, and (c) a ketone when $R_{11}$ is an oxygen atom and ⋯⋯ between $C_{11}$ and $R_{11}$ is a double bond;

$R_{20}$ is alkyl of 1 thru 4 carbon atoms or phenyl, the $R_{20}$'s can be the same or different;

$R_{21}$ is a hydrogen atom, —CO—$R_{21}'$ or —Si($R_{121}$)₃;

$R_{21}'$ is alkyl of 1 thru 4 carbon atoms or phenyl;

$R_{121}$ is alkyl of 1 thru 4 carbon atoms or phenyl, the $R_{121}$'s can be the same or different;

~ indicates that the attached group can be in either the α or β configuration;

⋯⋯ is a single or double bond;

TMS refers to trimethylsilyl;

THP refers to tetrahydropyranyl;

EEE refers to (1-ethoxy) ether ethyl [—O—CH(CH₃)OCH₂CH₃].

(30) A process according to Enumerated Embodiment 28 where the methylating agent is selected from the group consisting of compounds of the formula CH₃Cu, (CH₃)₂CuM or CH₃MgQ where M is a lithium or magnesium ion and Q is a chlorine, bromine or iodine atom.

(31) A process according to Enumerated Embodiment 28 where the methylating agent is CH₃MgQ.

(32) A process according to Enumerated Embodiment 28 where the copper catalyst is a cupric salt selected from the group consisting of cupric acetate, cupric chloride, cupric propionate, or a cuprous salt selected from the group consisting of cuprous chloride, cuprous bromide, cuprous iodide and cuprous cyanide and complexes thereof.

(33) A process according to Enumerated Embodiment 28 where the copper catalyst is cupric acetate.

(34) A process according to Enumerated Embodiment 28 where the silylating agent is selected from the group consisting of (R₂₀)₃ Si-E, bistrimethylsilylacetamide, where E is a chlorine, bromine or iodine atom or —NRαRβ where Rα and Rβ may be the same or different and are alkyl of 1 thru 5 carbon atoms or phenyl and where Rα and Rβ can be connected or cyclized in a ring with or without an oxygen or additional nitrogen atom and where R₂₀ is defined in Enumerated Embodiment 28.

(35) A process according to Enumerated Embodiment 28 where the silylating agent is trimethylsilyl chloride.

(36) A process according to Enumerated Embodiment 28 where the 16-unsaturated corticoid (I) is selected from the group consisting of 21-hydroxypregna-1,4,9(11),16-tetraene-3,20-dione 21-acetate or 9β,11β-epoxy-21-hydroxypregna-1,4,16-triene-3,20-dione 21-acetate.

(37) A process for the preparation of a 17α,20-epoxide of the formula

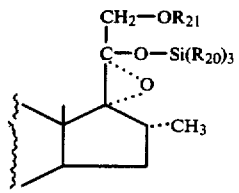

which comprises contacting a $\Delta^{17(20)}$-steroid of the formula

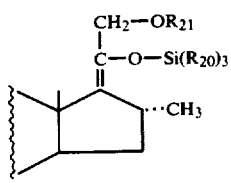
(II)

with a peracid where
R$_{20}$ is alkyl of 1 thru 4 carbon atoms or phenyl, the R$_{20}$'s can be the same or different;
R$_{21}$ is a hydrogen atom, —CO—R$_{21}'$ or —Si(R$_{121}$)$_3$;
R$_{21}'$ is alkyl of 1 thru 4 carbon atoms or phenyl;
R$_{121}$ is alkyl of 1 thru 4 carbon atoms or phenyl, the R$_{121}$'s can be the same or different.

(38) A process according to Enumerated Embodiment 37 where the $\Delta^{17(20)}$-steroid (II) is selected from the group consisting of $\Delta^4$-3-keto steroids (A)

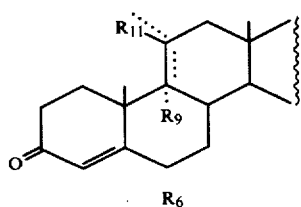

$\Delta^{1,4}$-3-keto steroids (B)

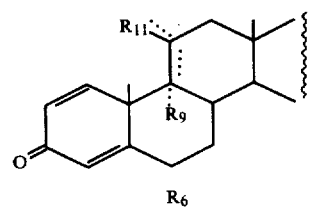

and 3$\beta$-hydroxy-$\Delta^5$ steroids (C)

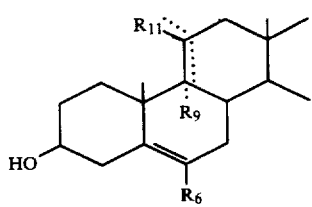

and the C$_3$ protected forms of the 3$\beta$-hydroxy-$\Delta^5$ (C) steroid (Cb)

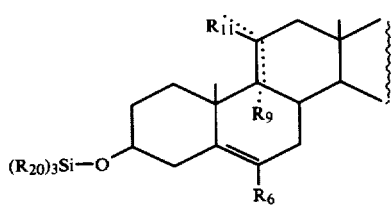

(Cc)

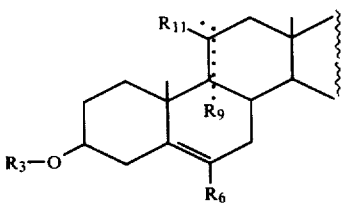

(Cd)

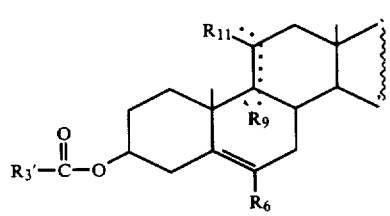

where
R$_3$ is alkyl of 1 thru 3 carbon atoms, a TMS, THP, or EEE group;
R$_3'$ is alkyl of 1 thru 5 carbon atoms or phenyl;
R$_6$ is a hydrogen of fluorine atom or methyl group;
R$_9$ is nothing, a hydrogen, fluorine or oxygen atom which makes the C ring
(a) $\Delta^{9(11)}$ when R$_9$ is nothing and
(b) 9$\beta$,11$\beta$-epoxide when R$_9$ and R$_{11}$ taken together are an oxygen atom; ~
R$_{11}$ is a hydrogen or oxygen atom, two hydrogen atoms, or $\alpha$- or $\beta$-hydroxyl group or trimethylsilyl ether thereof which makes the C-ring
(a) $\Delta^{9(11)}$ when R$_{11}$ is a hydrogen atom,
(b) 9$\beta$, 11$\beta$-epoxide when R$_9$ and R$_{11}$ taken together are an oxygen atom and ~ between C$_{11}$ and R$_{11}$ is a single bond, and
(c) a ketone when R$_{11}$ is an oxygen atom and ~ between C$_{11}$ and R$_{11}$ is a double bond;
R$_{20}$ is alkyl of 1 thru 4 carbon atoms or phenyl, the R$_{20}$'s can be the same or different;
R$_{21}$ is a hydrogen atom, —CO—R$_{21}'$ or —Si(R$_{121}$)$_3$;
R$_{21}'$ is alkyl of 1 thru 4 carbon atoms or phenyl;
R$_{121}$ is alkyl of 1 thru 4 carbon atoms or phenyl, the R$_{121}$'s can be the same or different;
~ indicates that the attached group can be in either the $\alpha$ or $\beta$ configuration;
~ is a single or double bond;
TMS refers to trimethylsilyl;
THP refers to tetrahydropyranyl;
EEE refers to ethoxy ethyl ether [—O—CH(CH$_3$)OCH$_2$CH$_3$].

(39) A process according to Enumerated Embodiment 37 where the peracid is selected from the group consisting of peracetic, perbenzoic, m-chloroperbenzoic.

(40) A 17$\alpha$,20-epoxy steroid according to Enumerated Embodiment 10 which is 17$\alpha$,20-epoxy-20,21-dihydroxy-16$\alpha$-methylpregna-1,4,9(11)-trien-3-one 20-trimethylsilyl ether 21-acetate; 9$\beta$,11$\beta$;17$\alpha$,20-diepoxy-20,21-dihydroxy-16$\alpha$-methylpregna-1,4-dien-3-one 20-trimethylsilyl ether 21-acetate and 17$\alpha$,20-epoxy-9$\alpha$-fluoro-11$\beta$,20,21-trihydroxy-16$\alpha$-methylpregna-1,4-dien-3-one 11,20-bis(trimethylsilyl)ether 21-acetate.

We claim:
1. A $\alpha^{17(20)}$-corticoid of the formula

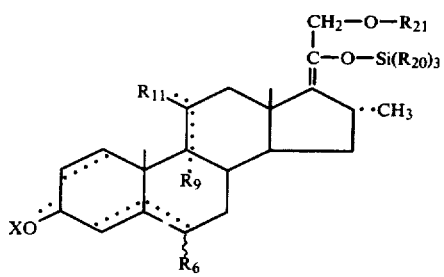

(II A-C)

and the C₃ protected forms of the 3β-hydroxy-Δ⁵-(C) A-ring where

R₆ is a hydrogen or fluorine atom or methyl group;

R₉ is nothing, a hydrogen, fluorine or oxygen atom which makes the C ring
(a) Δ⁹⁽¹¹⁾ when R₉ is nothing and
(b) 9β,11β-epoxide when R₉ and R₁₁ taken together are an oxygen atom;

R₁₁ is a hydrogen or oxygen atom, two hydrogen atoms, or α- or β-hydroxyl group or trimethylsilyl ether thereof which makes the C-ring
(a) Δ⁹⁽¹¹⁾ when R₁₁ is a hydrogen atom,
(b) 9β,11β-epoxide when R₉ and R₁₁ taken together are an oxygen atom and ∷∷∷ between C₁₁ and R₁₁ is a single bond, and
(c) a ketone when R₁₁ is an oxygen atom and∷∷∷ between C₁₁ and R₁₁ is a double bond;

R₂₀ is alkyl of 1 thru 4 carbon atoms or phenyl, the R₂₀s can be the same or different;

R₂₁ is a hydrogen atom, —CO—R₂₁′ or —Si(R₁₂₁)₃;

R₁₂₁′ is alkyl of 1 thru 4 carbon atoms or phenyl;

R₁₂₁ is alkyl of 1 thru 4 carbon atoms or phenyl, and R₁₂₁s can be the same or different;

~ indicates that the attached group can be in either the α or β configuration;

∷∷∷ is a single or double bond; and

X is a hydrogen atom or nothing; when X is nothing the ∷∷∷ at C₃ is a double bond and when X is a hydrogen atom the ∷∷∷ at C₃ is a single bond.

2. A Δ¹⁷⁽²⁰⁾-corticoid according to claim 1 where the Δ¹⁷⁽²⁰⁾-corticoid (II A-C) is a Δ⁴-3-keto (A) or Δ¹,⁴-3-keto (B) steroid.

3. A Δ¹⁷⁽²⁰⁾-corticoid according to claim 1 where the Δ¹⁷⁽²⁰⁾-corticoid (II A-C) is a 3β-hydroxy-Δ⁵(C) steroid in the free form

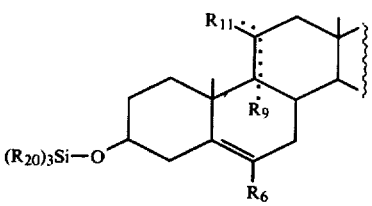

(Ca)

or C₃ protected from selected from the group consisting of

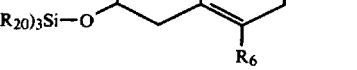

(Cb)

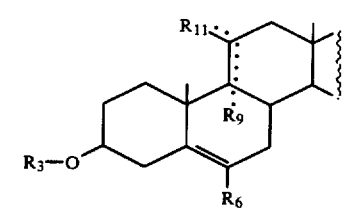

(Cc)

(Cd)

where

R₃ is alkyl of 1 thru 3 carbon atoms, a TMS, THP or EEE group;

R₃′ is alkyl of 1 thru 5 carbon atoms or phenyl;

where R₆, R₉, R₁₁, R₂₀, and ∷∷∷ are defined in claim 1.

4. A Δ¹⁷⁽²⁰⁾-corticoid according to claim 1 wherein R₆ is a hydrogen atom.

5. A Δ¹⁷⁽²⁰⁾-corticoid according to claim 1 where R₉ is nothing or an oxygen atom and where R₁₁ is a hydrogen atom or an oxygen atom making the C-ring Δ⁹⁽¹¹⁾ or a 9β,11β-epoxide.

6. A Δ¹⁷⁽²⁰⁾-corticoid according to claim 1 where R₂₀ is selected from the group consisting of methyl, isopropyl, t-butyl or phenyl.

7. A Δ¹⁷⁽²⁰⁾-corticoid according to claim 1 where R₂₀ is methyl or phenyl.

8. A Δ¹⁷⁽²⁰⁾-corticoid according to claim 1 where R₂₁ is —CO—R₂₁′ and R₂₁′ is selected from the group consisting of methyl, ethyl or phenyl.

9. A Δ¹⁷⁽²⁰⁾-corticoid according to claim 1 which is selected from the group consisting of 20,21-dihydroxy-16α-methylpregna-1,4,9(11),17(20)-tetraen-3-one 20-trimethylsilyl ether 21-acetate, 9β,11β-epoxy-20,21-dihydroxy-16α-methylpregna-1,4,17(20)-trien-3-one 20-trimethylsilyl ether 21-acetate and 9α-fluoro-11β,20,21-trihydroxy-16α-methylpregna-1,4,17(20)-trien-3-one 11,20-bis(trimethylsilyl)ether 21-acetate.

* * * * *

UNITED STATES PATENT OFFICE
CERTIFICATE OF CORRECTION

Patent No. 4,704,455

Dated November 3, 1987

Inventor(s) Verlan H. VanRheenen and Joel E. Huber

It is certified that error appears in the above-identified patent and that said Letters Patent are hereby corrected as shown below:

Column 1, line 27, "$\alpha^{17(20)}$-20-" should read -- -$\Delta^{17(20)}$-20- --

Column 6, line 24, "$R_{20}4Os$" should read -- $R_{20}$'s --

Column 13, Chart B (A), lines 22-23, "  " should read -- 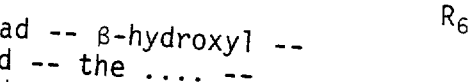 --

Column 14, line 48, "β-hydroxy" should read -- β-hydroxyl --

Column 14, line 67, "the ___" should read -- the .... --

Column 16, line 13, "-triene-" should read -- -trien- --

Column 16, line 46, "and ___" should read -- and .... --

Column 17, line 5, (Ca), "  " should read --  --

Column 17, line 18, (Cb), "  " should read --  --

Column 21, (Cb), lines 16-17, " 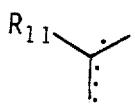 " should read --  --

UNITED STATES PATENT OFFICE
CERTIFICATE OF CORRECTION

Patent No. 4,704,455

Dated November 3, 1987

Inventor(s) Verlan H. VanRheenen and Joel E. Huber

It is certified that error appears in the above-identified patent and that said Letters Patent are hereby corrected as shown below:

Column 21, line 61, "and ___" should read -- and ..... --
Column 22, line 9, "ether ethyl" should read -- ethyl ether --
Column 23, (A), line 30, "∨" should read --  --

Column 23, (B), line 42, "∨" should read --  --

Column 24, line 32, " ;...." should read -- ;       --
Column 26, line 1, "protected from" should read -- protected form --
Column 24, line 68, "$\alpha^{17(20)}$-" should read -- $\Delta^{17(20)}$- --

Signed and Sealed this

Fourteenth Day of June, 1988

Attest:

DONALD J. QUIGG

Attesting Officer

Commissioner of Patents and Trademarks